(12) United States Patent
Booth et al.

(10) Patent No.: US 8,537,215 B2
(45) Date of Patent: Sep. 17, 2013

(54) MULTI-CAMERA SKIN INSPECTION SYSTEM FOR EXTRUDED CERAMIC HONEYCOMB STRUCTURES

(75) Inventors: Robertson Dewhurst Booth, Elmira, NY (US); Uta-Barbara Goers, Campbell, NY (US)

(73) Assignee: Corning Incorporated, Corning, NY (US)

(*) Notice: Subject to any disclaimer, the term of this patent is extended or adjusted under 35 U.S.C. 154(b) by 535 days.

(21) Appl. No.: 12/956,055

(22) Filed: Nov. 30, 2010

(65) Prior Publication Data
US 2011/0128370 A1 Jun. 2, 2011

Related U.S. Application Data (60) Provisional application No. 61/265,122, filed on Nov. 30, 2009.

(51) Int. Cl.
*H04N 7/18* (2006.01)
*G06K 9/00* (2006.01)

(52) U.S. Cl.
USPC ........... 348/125; 348/128; 348/133; 348/134; 382/141; 356/237.1

(58) Field of Classification Search
USPC ................. 348/125, 128, 133, 134; 382/141; 356/237.1
See application file for complete search history.

(56) References Cited

U.S. PATENT DOCUMENTS

| | | | | |
|---|---|---|---|---|
| 6,820,022 B2* | 11/2004 | Popp et al. | | 702/81 |
| 7,212,228 B2* | 5/2007 | Utsumi et | | 348/139 |
| 7,283,224 B1* | 10/2007 | Smithgall | | 356/237.1 |
| 8,090,143 B2* | 1/2012 | Komaki et al. | | 382/100 |
| 8,421,857 B2* | 4/2013 | Akao et al. | | 348/92 |
| 2002/0109112 A1* | 8/2002 | Guha et al. | | 250/559.46 |
| 2003/0112437 A1* | 6/2003 | Enomoto et al. | | 356/402 |
| 2003/0174320 A1* | 9/2003 | Yokoyama et al. | | 356/237.6 |
| 2006/0174695 A1* | 8/2006 | Miyashita et al. | | 73/38 |
| 2007/0091309 A1* | 4/2007 | Kondo | | 356/364 |
| 2009/0010523 A1* | 1/2009 | Komaki et al. | | 382/141 |
| 2009/0091615 A1* | 4/2009 | Tan et al. | | 348/125 |
| 2010/0238281 A1* | 9/2010 | Akao et al. | | 348/92 |
| 2011/0128370 A1* | 6/2011 | Booth et al. | | 348/125 |

FOREIGN PATENT DOCUMENTS
EP 2 006 666 12/2008

* cited by examiner

*Primary Examiner* — Chikaodili E Anyikire
(74) *Attorney, Agent, or Firm* — Charles A. Greene (57) ABSTRACT

A multi-camera skin inspection system for inspecting the outer skin and the skin perimeter of extruded ceramic honeycomb structures is disclosed. The system has a camera that captures first digital line images of a line-illuminated portion of the outer skin as the ceramic honeycomb structure rotates to form a scanned digital image of the outer skin. The system also has second and third cameras that respectively capture second and third digital line images of illuminated first and second endfaces, including the corresponding first and second skin perimeters, as the ceramic honeycomb structure rotates to form scanned digital images of the ceramic honeycomb structure perimeters. The system also forms a composite image from the three scanned images and identifies at least one defect in the ceramic honeycomb structure from the composite image.

20 Claims, 10 Drawing Sheets

MULTI-CAMERA SKIN INSPECTION SYSTEM FOR EXTRUDED CERAMIC HONEYCOMB STRUCTURES

CROSS REFERENCE TO RELATED APPLICATION

This application claims the benefit of priority to U.S. Provisional Application No. 61/265,122, filed on Nov. 30, 2009.

FIELD

This disclosure generally relates to systems and methods for inspecting structures, and in particular to a multi-camera system for inspecting the skin and perimeter of an extruded ceramic honeycomb structure.

BACKGROUND

Ceramic honeycomb structures are used in vehicular exhaust systems to reduce pollutants. Such structures are generally formed by extrusion and comprise a network of interconnected web walls that form a matrix of elongated, gas-conducting cells which may be square, octagonal or hexagonal in shape, for example. The network of web walls is surrounded by a cylindrical outer wall or "skin" that is integrally connected to the outer edges of the web walls to form a cylindrical structure having opposing inlet and outlet endfaces for receiving and expelling exhaust gases through the matrix of cells.

The outer skin and the perimeter at each end of a ceramic honeycomb structure need to be inspected to ensure the structure meets specification with respect to skin thickness and uniformity, and the absence or presence of defects such as cracks, fissures, and skin separation (delamination) and the like.

Consequently, improved systems and methods that can quickly and efficiently inspect ceramic honeycomb structures are needed.

SUMMARY

An aspect of the disclosure is a system for inspecting a ceramic honeycomb structure for at least one defect, wherein the ceramic honeycomb structure has an outer skin and opposite first and second endfaces having respective first and second perimeters. The system includes a movable stage that moves the ceramic honeycomb structure relative to a line illumination of the outer skin, and first and second line illuminations of respective first and second portions of the first and second endfaces, including the respective first and second perimeters. The system also includes a first line-scan camera that captures a scanned image of the illuminated line portion of the outer skin. In an example, this illuminated line portion extends from end to end. The system further includes second and third line-scan cameras that capture respective scanned images of the first and second illuminated line portions of the first and second endfaces, including the first and second perimeters, onto respective second and third detectors. The system also includes a controller operatively configured to control the movable stage to effectuate movement of the ceramic honeycomb structure and to receive the first, second and third lines images and form therefrom a composite scanned image.

Another aspect of the disclosure is a method of inspecting a ceramic honeycomb structure for at least one defect, wherein the ceramic honeycomb structure has an outer skin and opposite first and second endfaces having respective first and second perimeters. The method includes capturing first digital line images of a line-illuminated portion of the outer skin as the ceramic honeycomb structure rotates to form a scanned digital image of the outer skin. The method also includes capturing second and third digital line images of line-illuminated first and second endfaces, including the respective first and second perimeters, as the ceramic honeycomb structure rotates to form first and second scanned digital images. The method further includes forming a composite image from the first, second and third scanned images, and then identifying at least one defect from the composite image.

Another aspect of the disclosure is a system for inspecting a ceramic honeycomb structure for at least one defect, wherein the ceramic honeycomb structure has an outer skin and opposite first and second endfaces having respective first and second perimeters. The system includes a first line-scan camera unit having a limited depth of field. This line-scan camera unit captures a first scanned image of a line-illuminated portion of the outer skin as the ceramic honeycomb structure rotates while maintaining the line-illuminated skin portion within the depth of field and perpendicular to the first line-scan camera's viewing direction. The system also includes second and third line-scan camera units to capture respective second and third scanned images of line-illuminated first and second endface portions, including the respective first and second perimeters, as the ceramic honeycomb structure rotates. The system also includes a transport system to transport and rotate the ceramic honeycomb structure. The system has a controller operatively configured to control the transport system and to receive the first, second and third scanned images and form therefrom a composite scanned image.

It is to be understood that both the foregoing general description and the following detailed description present embodiments of the disclosure, and are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure and, together with the description, serve to explain the principles and operations of the disclosure.

DETAILED DESCRIPTION

Reference is now made in detail to embodiments of the disclosure, examples of which are illustrated in the accompanying drawings. Whenever possible, the same or analogous reference numbers are used throughout the drawings to refer to the same or like parts.

Ceramic Honeycomb Structures

Figure 1:
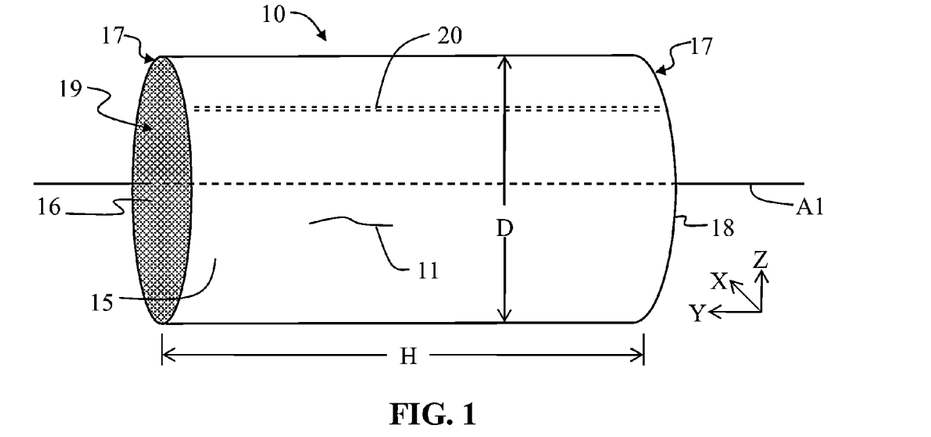
FIG. 1 is an isometric view of an example ceramic honeycomb structure.
Figure 2:
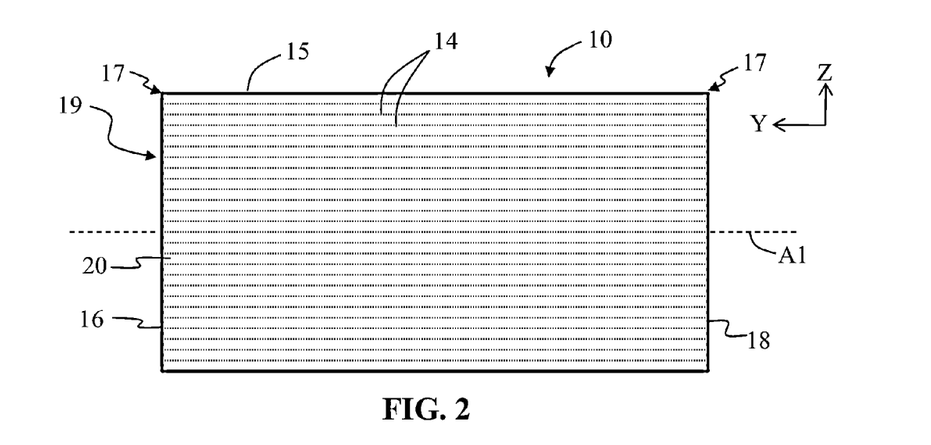
FIG. 2 is a side view of the ceramic honeycomb structure of FIG. 1.
Figure 3:
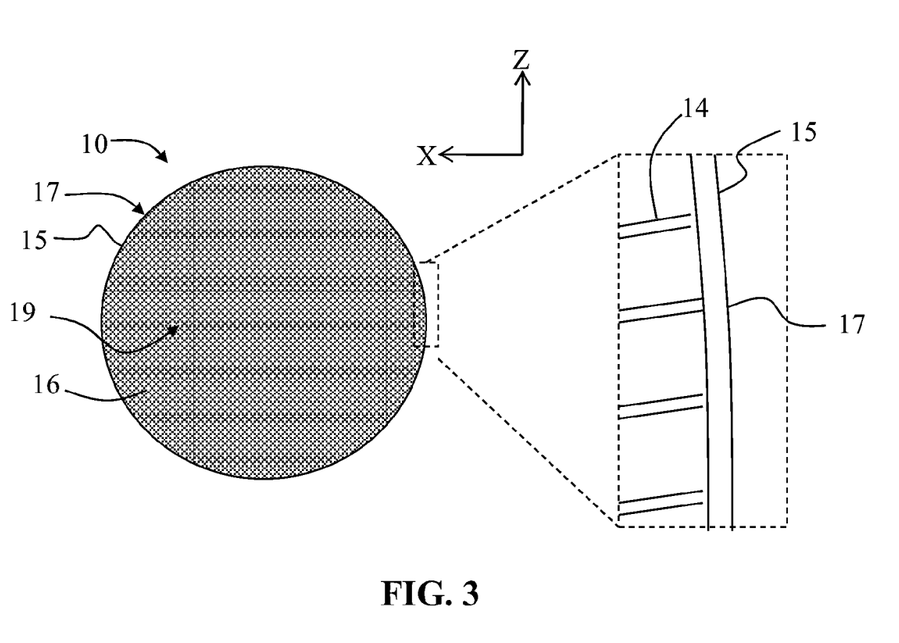
FIG. 3 is an end-on view of the ceramic honeycomb structure of FIG. 1 that includes a close-up view of the outer skin and the adjacent cell walls.

FIG. 1 is an isometric view of an example ceramic honeycomb structure 10. FIG. 2 is a side view of the ceramic honeycomb structure 10 of FIG. 1, and FIG. 3 is an end-on view that includes a close-up view shown in the inset. Cartesian X-Y-Z coordinates are shown for the sake of reference. Ceramic honeycomb structure 10 has a central axis A1 that defines an axial (longitudinal) direction. Ceramic honeycomb structure 10 includes a matrix of intersecting, thin, porous walls 14 surrounded by an outer skin 15. Walls 14 extend across and between opposing endfaces 16 and 18, and form a large number of adjoining hollow passages or "cells" 20 that also extend between, and are open at, the endfaces. Outer skin 15 has respective perimeters 17 at endfaces 16 and 18, with the perimeters each having the same general contour shape, such as circular or oval. The intersecting walls 14 at endfaces 16 and 18 form a "web" 19, and walls 14 constitute "web walls." Ceramic honeycomb structure 10 has a diameter D and a height H as measured between endfaces 16 and 18. Ceramic honeycomb structure 10 can be either "green" (i.e., newly extruded) or "fired" (i.e., sintered).

In an example embodiment, ceramic honeycomb structure 10 has, for example, between 100 to 900 cells per square inch, which translates into a cell width that can range from between about 2.5 mm to about 0.85 mm. Walls 14 of such a ceramic body 10 can be rendered quite thin, e.g., on the order of 2-10 mils thick. Other filter types (e.g., smoke-stack filters) utilize ceramic honeycomb structures 10 having on the order of 50 cells per square inch, which translates into a cell width of about 3.6 mm.

In some applications, cells 20 are completely open between endfaces 16 and 18. Here, the cell density may be maximized to maximize the area of contact between the automotive exhaust gases that flow directly through gas-conducting cells 20. To reduce the pressure drop that the flow-through catalyst imposes on the exhaust gases, walls 14 can be rendered quite thin, i.e. on the order of 2-10 mils.

When ceramic honeycomb structures 10 are plugged and used as particulate filters, such as diesel particulate filters, the open ends of cells 20 at the inlet and outlet endfaces 16 and 18 are plugged in a "checkerboard" pattern to force the engine exhaust gases to pass through the porous walls 14 before exiting endface 18. The density of cells 20 in particulate filters can be lower than for catalytic converters, e.g. about 100 to 400 cells per square inch. Further, walls 14 are generally thicker, on the order of 10-25 mils thick, for example. Whether ceramic honeycomb structures 10 are used as a catalyst support or a particulate filter, the outer skin 15 can be thicker, and in some cases can be many times as thick as walls 14.

Ceramic honeycomb structures 10 can be manufactured by extruding a plasticized ceramic forming precursor of cordierite, mullite, silicon carbide or aluminum titanate through an extrusion die. The extruded "green body" is then cut and dried. Such green bodies are quite fragile, and are transported to a kiln, where the resultant heat transforms the relatively soft and fragile green body into a hardened, fired honeycomb structure.

During the manufacturing process, defects 11 may occur in ceramic honeycomb structure 10. Such defects 11 include, for example, skin thickness and uniformity being outside of the specification, as well as cracks, fissures (FIG. 1 and FIG. 6), skin separation (delamination) (FIG. 6) and the like. These defects might potentially impact the structural integrity of ceramic honeycomb structure 10 and influence the performance of the particular device formed from the structure.

Multi-Camera Skin Inspection System

Figure 4:
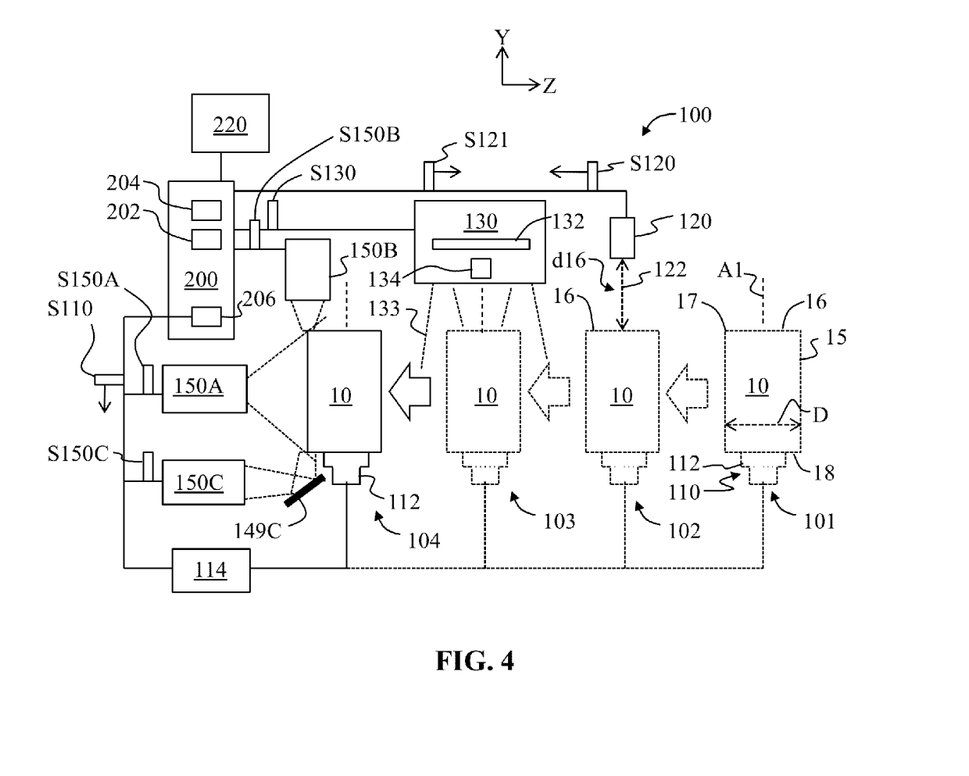
FIG. 4 is a schematic diagram of an example embodiment of a multi-camera skin inspection system for inspecting the outer skin and end perimeters of a ceramic honeycomb structure.

FIG. 4 is a schematic diagram of an example embodiment of a multi-camera skin inspection system ("system") 100 for inspecting skin 15 and perimeters 17 of ceramic honeycomb structure 10. System 100 includes stations 101 through 104 and a transport system 110 that includes a stage 112 and that supports and moves ceramic honeycomb structure 10 between the stations and positions the structure within each station. Transport system 110 includes a stage driver 114 operably coupled to stage 112 and configured to move the stage in X and Z directions, as well as cause the stage to rotate, as described below.

Station 101 is a mounting station where ceramic honeycomb structure 10 is placed on stage 112. In an example embodiment, the top portion of stage 112 includes a round plate having a diameter smaller than the diameter D of ceramic honeycomb structure 10 so that endface 18 hangs over the outer edge of the stage. This allows for perimeter 17 of skin 15 to be accessed for inspection, as described below. Station 101 also includes a centering mechanism (not shown) that centers the honeycomb structure 10 on stage 112.

Station 102 is a height-measuring station that measures the relative height H of ceramic honeycomb structure 10 relative to stage 112 (by measuring distance d16) so that the vertical stand-alone translation stage 159 (introduced and discussed below in connection with FIG. 7) of transport system 110 can properly position movable line-scan camera unit 150B (introduced and discussed below) within station 104. An example height-measuring station 102 includes a laser-based distance measuring device 120 that emits a laser beam 122 that strikes endface 16 when ceramic honeycomb structure 10 is moved into position. Distance measuring device 120 receives a reflected portion of the laser beam 122 from the endface 16 and generates a signal S120 representative of distance d16. This distance is readily converted into height H by knowing the vertical coordinate of the top surface of stage 112. Distance d16 is used for accurately placing a contour camera 134 and line-scan camera 150B at the proper working distance to endface 16 of ceramic honeycomb structure 10 within respective inspection stations 103 and 104.

Station 103 is a contour-imaging station that includes a contour-imaging unit 130 having a light source 132 to illuminate endface 16 and a contour-imaging camera 134 to capture a digital image of the endface, including skin perimeter 17, so that the controller can determine the contour (perimeter) shape of the particular ceramic honeycomb structure 10 to be inspected. An example contour-imaging station 103 includes a ring-shaped light source 132 and a centrally arranged contour-imaging camera 134. Contour imaging unit 130 sends a signal S130 representative of the captured perimeter image to a controller 200 (introduced and discussed below), which is configured (e.g., programmed) to distinguish between round and non-round (e.g., oval) contours. For round contours, the best-fitting circle is used to describe the shape of the imaged perimeter 17. For oval contours, the perimeter data are retrieved from a previously created database in controller 200. In an example embodiment, light 133 from light source 132 that is not incident upon endface 16 does not return to contour-imaging camera 134 so that the portion of the captured image beyond perimeter 17 is dark.

Figure 5:
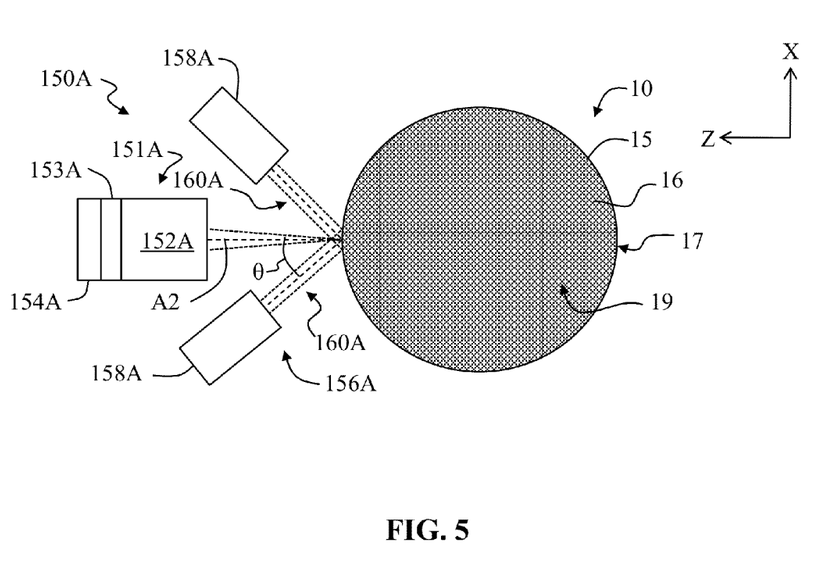
FIG. 5 is a top-down view of the inspection station of the multi-camera skin inspection system of FIG. 4, showing only the line-scan camera unit that captures an image of the outer skin surface.
Figure 6:
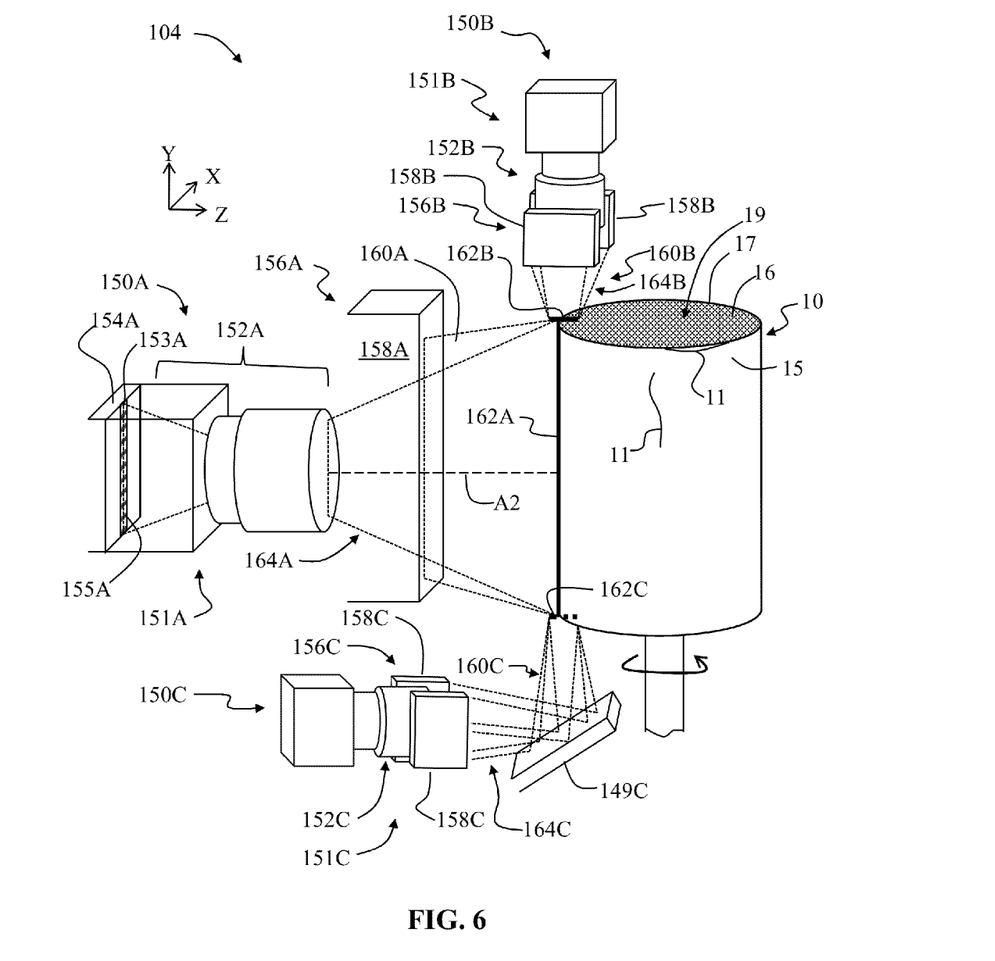
FIG. 6 is a side perspective view of the inspection station of the multi-camera skin inspection system of FIG. 4, showing all three line-scan camera units.
Figure 7:
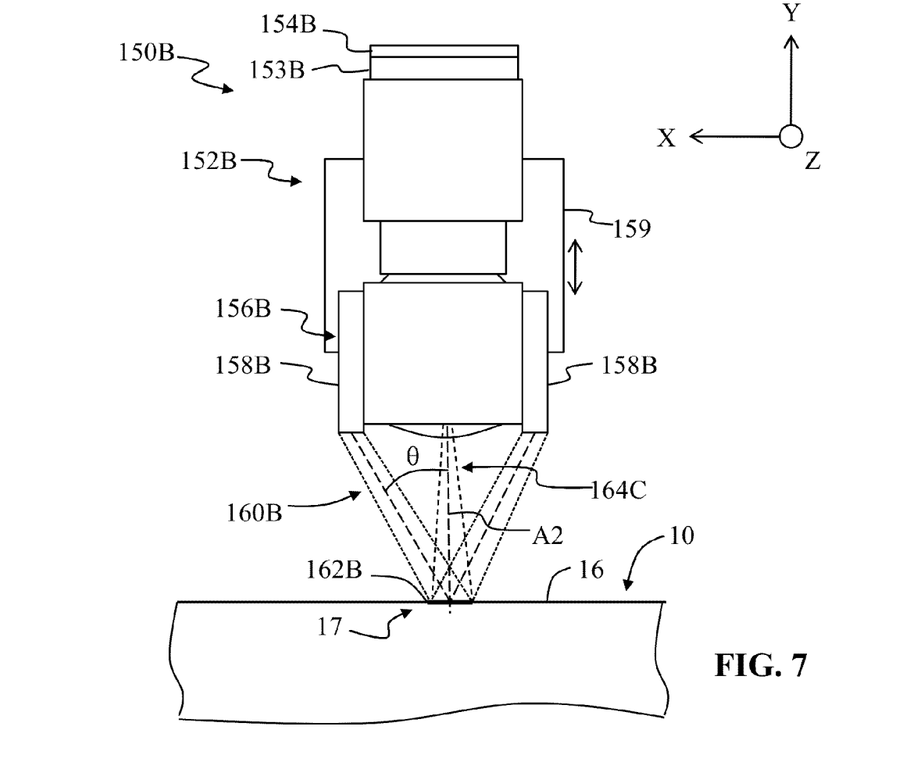
FIG. 7 is a close-up side view of an example line-scan camera unit for imaging the skin perimeter at one of the endfaces of the ceramic honeycomb structure.

Station 104 is an optical inspection station where the inspection of outer skin 15 and perimeters 17 is performed by capturing a side-view and two endface-view images. Optical inspection station 104 includes three line-scan camera units 150, namely 150A, 150B and 150C that are configured to "grab" digital images and to send respective electrical signals S150A, S150B and S150C to a controller 200. As ceramic honeycomb structure 10 rotates on stage 112, line-scan camera unit 150A is adapted (e.g., programmed) to capture an image of outer skin 15 (i.e., the outer skin surface, as opposed to the outer skin perimeter 17). Simultaneously, line-scan camera units 150B and 150C are respectively configured to capture scanned images of the outer edge of endfaces 16 and 18 traveling along perimeter 17. Line-scan cameras 150 each have a central axis A2 (FIG. 5, FIG. 6 and FIG. 7).

System 100 also includes the aforementioned controller 200, which is operably connected to transport system 110, to line-scan camera units 150A, 150B and 150C, to contour imaging unit 130, and to height-measuring device 120. Controller 200 is configured to control the general operation of system 100. Controller 200 is or includes a computer, such as a workstation, that includes a processor unit 202 having one or more processors with image-processing capability (e.g., image-processing software) embodied in a computer-readable medium such as a memory unit 204. Memory unit 204 can be any of the known types of memory used for storing information (especially digital information stored in any one of the image file types such as TIFF, JPEG, etc.) for use by computers or processors, including solid-state memory, a RAM disk, or optical-disk memory. Controller 200 may also include a microcontroller unit 206 that includes a device for interfacing with and controlling the operation of transport system 110. In an example embodiment, memory unit 204 stores instructions (e.g., image processing and/or image analysis software) that cause processor unit 202 to carry out the image-processing methods described below.

An example image-processing and image analysis software for controller 200 is the WiT software package (e.g., WiT 8.2) from Dalsa Digital Imaging Co., Burnaby BC, Canada. In an example embodiment, digital images are captured with line-scan camera units 150A, 150B, and 150C using three frame-grabber boards (one per camera) and an imaging library. Each image consists of four files (e.g., TIFF files), which are stored (e.g., instantly stored) in memory unit 204.

System 100 further includes a display unit 220 connected to controller 200 and configured to display numeric, alphanumeric, and graphical information of the type discussed in detail below. A typical display unit 220 has limited resolution (e.g., 1920×1200 pixels) as compared to the captured digital images (e.g., 550 Megapixels), so in an example embodiment the image processing carried out by controller 200 enhances the visibility of defects 11 in the captured images while reducing the amount of information obtained. This allows the images to be displayed in a manner that effectively conveys the relevant inspection information.

FIG. 5 is a top-down view of station 104, showing only line-scan camera unit 150A. FIG. 6 is a side perspective view of station 104, showing all three line-scan camera units 150A, 150B and 150C (but with one of the line illuminators 158A not shown for ease of illustration). In an example embodiment, the line-scan cameras 150A, 150B and 150C have intersecting fields of view (FOV). In an example embodiment, the imaged lines of all three line-scan camera units 150A, 150B and 150C are in the same plane (e.g., a radial slice through the ceramic honeycomb structure), as shown in FIG. 6. Note that line-scan camera 150C makes use of a folding mirror 149C so that the camera can be arranged horizontally along the Z-direction while viewing endface 18 along the Y-direction. The use of folding mirror 149C serves to make system 100 more compact.

Figure 8:
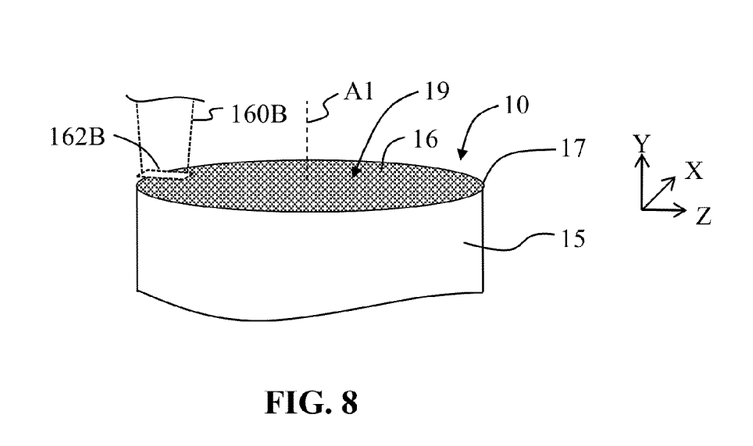
FIG. 8 is a perspective view of an endface of the ceramic honeycomb structure showing an example illumination line that is generally radial relative to the ceramic honeycomb structure axis and that slightly overlaps the endface perimeter.

FIG. 7 is a close-up side view (looking in the Z-direction) of an example line-scan camera unit 150B imaging a line portion of endface 16. Line-scan camera unit 150B is mounted to a vertical translation stage 159 operably connected to controller 200 and that provides motion along Y-axis of transport system 110. FIG. 8 is a perspective view of endface 16 showing an example illumination line 162B that is generally radial relative to axis A1 of ceramic honeycomb structure 10 and that slightly extends beyond perimeter 17. Note that the portion of light from illumination line 162B that is outside of perimeter 17 is generally not reflected back so that the image formed by line-scan camera unit 150B is dark outside of perimeter 17. An example illumination angle θ between the illumination beams 160 and the line-scan camera central axis A2 is between 30° and 35°.

Each line-scan camera unit 150 includes a line-scan camera 151 having an imaging lens 152, a line-scan image sensor 153 formed from a linear array of pixels 155 (FIG. 6) and image-sensor electronics 154 that include, for example, a frame-grabber board with a hardwire trigger. Image sensor electronics 154 may also be located in controller 200. Line-scan camera units 150 also include a line-illumination system 156 that includes two line illuminators 158 located on either side of line-scan camera 151. In an example embodiment, imaging lenses 152B and 152C may be telecentric lenses.

With reference again to FIG. 5 and FIG. 6, line illumination system 156A generates two optical line beams 160A that converge and overlap to form an illumination line 162A on skin 15 of ceramic honeycomb structure 10. In an example embodiment, illumination line 162A has a length equal to or slightly greater than height H of ceramic honeycomb structure 10 so that the entire height of outer skin 15 is illuminated. Likewise, with reference to FIG. 6, line illumination systems 156B and 156C generate respective optical line beams 160B and 160C that respectively form illumination lines 162B and 162C on respective endfaces 16 and 18 across corresponding perimeters 17. In an example embodiment, illumination lines 162B and 162C have a length of about 0.5 inches (i.e., about 1.25 cm). The use of two illumination lines 160 that converge and overlap to form a single illumination line 162 improves illumination uniformity and thus improves imaging quality. Line-scan camera units 150 have respective field of views 164 (i.e., 164A, 164B and 164C) that correspond to their respective illumination lines 162 formed on ceramic honeycomb structure 10. Thus, in an example, the combined field of view of all three line-scan camera units 150 can be considered as a single field of view that covers the entire height H of skin 15 and that wraps around edges 16 and 18 to cover the respective perimeters 17.

Figure 9:
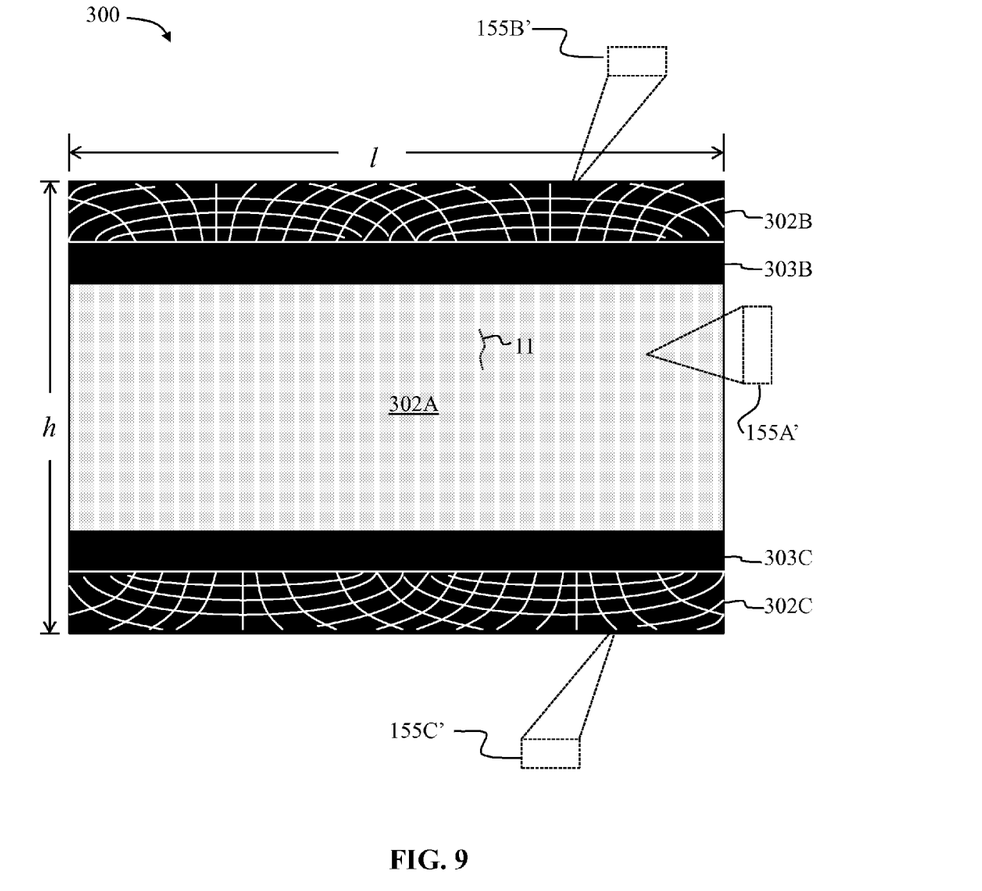
FIG. 9 is an schematic diagram of an composite image formed from the three scanned images captured by the three line-scan cameras of the multi-camera skin inspection system of FIG. 4.

An example line-scan image sensor 153A includes a linear array of pixels 155A (e.g., 8K pixels) that are 6 μm wide (FIG. 6). With reference also to FIG. 9 (introduced and discussed below), the horizontal width of the "scanned" pixel 155A' in scanned skin image 302A is determined by the rotational speed of ceramic honeycomb structure 10. In an example embodiment, the detection (resolution) limit for defects 11 is 12 μm, and the horizontal×vertical pixel resolution (e.g., scanned pixel size 155A') of the captured scanned image 302A is 12 μm×19 μm.

Example line-scan image sensors 153B and 153C include respective linear arrays of pixels 155B and 155C (e.g., 2K pixels) each being 4 μm an wide. The horizontal width of the scanned pixels 155B' and 155C' in the respective captured scanned perimeter images 302B and 302C (FIG. 9), which is determined by the rotational speed, is 12 μm. The horizontal× vertical image pixel resolution for scanned pixels 155B' and 155C' is thus 12 μm×6.5 μm, wherein the 6.5 μm is the pixel resolution of the captured scanned image relevant for measuring skin thickness and separation.

With reference again to FIG. 4, in the operation of system 100, a ceramic honeycomb structure 10 to be inspected is mounted on stage 112 in mounting station 101. This operation can be performed manually or robotically. Controller 200 then sends a control signal 5110 to transport system 110 to move stage 112 and the ceramic honeycomb structure 10 mounted thereon to height-measuring station 102. Controller 200 sends a control signal 5121 to laser measuring device 120 to initiate measurement of the height H of ceramic honeycomb structure (or the location of endface 16 in the Y-direction via distance d16) as mounted on stage 112 so that optical inspection station 104 can be appropriately configured to accommodate the structure. Laser measuring device 120 sends a signal 5120 containing the height measurement to controller 200. Controller 200 then sends another control signal 5110 to transport system 110 to cause stage 112 to move to contour measurement station 103, which illuminates and captures an image of perimeter 17 and sends a signal 5130 representative of the captured digital image of the perimeter to controller 200.

With continuing reference to FIG. 4, controller 200 sends another control signal 5110 to transport system 110 to cause stage 112 to move to optical inspection station 104. Controller 200 uses the height/distance information from height measurement station 102 and perimeter information from contour measurement station 103 to place line-scan camera units 150 and ceramic honeycomb structure 10 in proper position relative to each other. If necessary, controller 200 automatically adjusts the position of one or more of line-scan camera units 150 to accommodate ceramic honeycomb structure 10. In an example embodiment, only line-scan camera unit 150B is adjusted via vertical translation stage 159 to be positioned at the appropriate distance from endface 16.

Once ceramic honeycomb structure 10 is in its proper position in optical inspection station 104, controller 200 sends a control signal 5110 to transport system 110 to cause stage 112 to move in a manner that allows line-scan camera units 150 to capture their respective images of ceramic honeycomb structure 10. Information regarding the contour of perimeter 17 from contour measuring station 103 allows controller 200 to control the movement of transport system 110. In the case of a circular contour perimeter 17, controller 200 directs transport system 110 to cause stage 112 to rotate at a select rotational speed. Line-scan image sensors 153 in line-scan cameras 150 are synchronized to the stage rotational speed. In order for pixel resolution 155A', 155B' and 155C' in captured scanned images 302A, 302B, and 302C to be maintained, the image-capture rate (frame rate) of line-scan image sensors 153 is adjusted before each image capture to account for the diameter D of ceramic honeycomb structure 10. This allows line-scan camera unit 150A to capture a scanned image of the entire circumference of at least a portion of outer skin 15, and for line-scan camera units 150B and 150C to capture respective scanned images of the entire circumference of perimeters 17 at respective endfaces 16 and 18. The respective scanned images are embodied in the aforementioned electrical signals S150A, S150B and S150C, which are provided to controller 200.

When perimeter 17 has a circular or close to circular contour, the rotation of ceramic honeycomb structure 10 about its axis A1 does not significantly change the position of outer skin 15 relative to illumination lines 162. Thus, the captured images from line-scan camera unit 150A remain in focus, and there is no or very little "wobble" in the captured images formed by line-scan cameras 150B and 150C. However, when perimeter 17 has an oval or non-circular contour, then adjustments need to be made in the movement of stage 112 to keep outer skin 15 in focus and coincident with illumination line 162A and to keep the imaged portion of perimeters 17 traveling the same path through illumination lines 162B and 162C. An example embodiment of system 100 that is configured to handle non-circular perimeter contours is discussed in greater detail below.

Processor 202 in controller 200 combines the separately captured scanned images from line-scan camera units 150 to form a composite image 300, an example of which is shown in FIG. 9. Composite image 300 has a middle section 302A corresponding to outer skin 15 and two end sections 302B and 302C respectively corresponding to images of perimeter 17 at ends 16 and 18. The dark bands 303B and 303C in composite image 300 are due to the fact that light in illumination lines 162B and 162C that extends over perimeter 17 is not reflected back.

For an example ceramic honeycomb structure 10 having a diameter D=5.66 inches and a height H=6 inches, the image length l in pixels for a 12-micron pixel size p is given by $l=\pi D/p=\pi[5.66"] [2.54 \times 10^4 \mu m/inch]/[12 \mu m]=37,637$ pixels. The image height h in pixels is given by 2000+2000+8192=12,192. Thus, the total number N of pixels in the composite image 300 is given by N=(37,637)×(12,192)=459 Megapixels. This composite image represents a relatively high-resolution image that can reveal very small defects. In an example embodiment, composite image 300 is between about 250 Megapixels and about 500 Megapixels depending on the diameter D and height H of ceramic honeycomb structure 10.

Figure 10A:
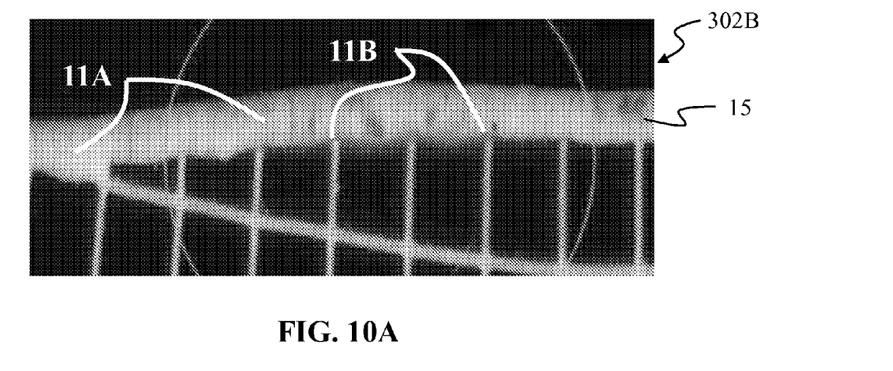
FIG. 10A and FIG. 10B are close-up views ("zoom views") of an actual portion of the skin perimeter image, illustrating examples of variations in the skin thickness.
Figure 10B:
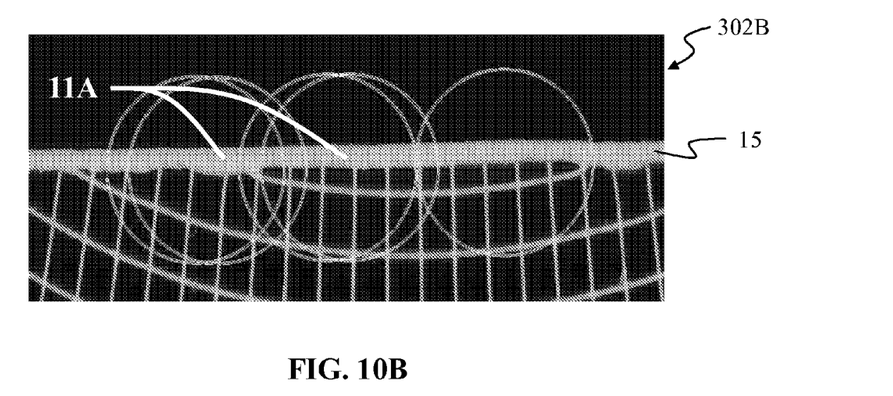

In an example embodiment, composite image 300 (or the separate images 302A, 302B and 302C) is acquired and analyzed at high-resolution to find defects 11. Defects 11 are then dilated or marked to make them visible in display 220. The composite image 300 (or the separate images) is reduced in pixel count by a predetermined factor (e.g., 4× reduction) before being displayed. A zoom function allows viewing of regions of interest at higher magnification. FIG. 10A and FIG. 10B are close-up views ("zoom views") of a portion of image 302B of skin perimeter 17 illustrating examples of defects such as skin thickness variations 11A and skin separation 11B in the skin 15. In an example embodiment, the image processing and analysis software is configured to find and highlight relatively large skin separation defects 11B (e.g., of greater than 50 μm) via a "coarse" algorithm, and relatively small skin separation defects (e.g., of greater than or equal to 12 μm) via a "fine" algorithm.

Figure 11A:
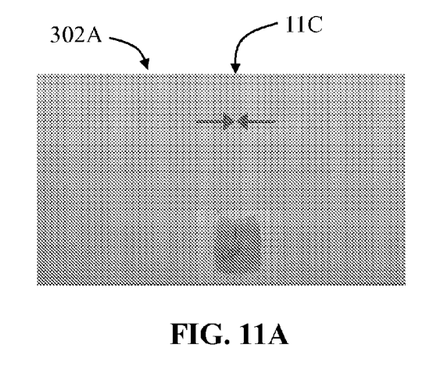
FIG. 11A and FIG. 11B are respective close-up photographic views of the skin image shown in original form and after image processing, illustrating how a crack in the skin can be seen after image processing.
Figure 11B:
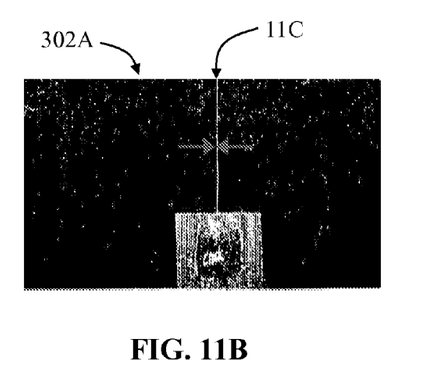

FIG. 11A and FIG. 11B are respective views of image 302A shown in original form and after image processing. Note that in the original form of FIG. 11A, the defect 11C is essentially invisible, whereas in the processed image of FIG. 11B, the defect 11C in the form of a line-type crack is clearly visible.

Oval Perimeter Contour

Figure 12:
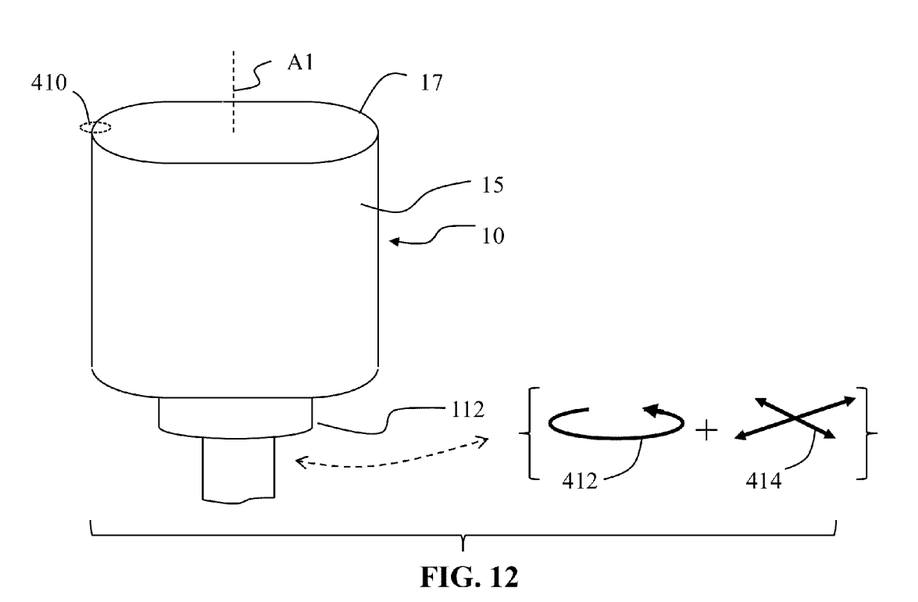
FIG. 12 is a schematic diagram showing an example ceramic honeycomb structure mounted upon a stage and having an oval shaped perimeter, and illustrating the combined rotation and translation motion that keeps the imaged portion of the skin within the depth of field and perpendicular to the viewing direction of the line-scan camera 150A that images the skin.

In the case where ceramic honeycomb structure 10 has an oval contour, stage 112 is driven to be simultaneously translated and rotated so that the imaged portion of skin 15 passes through the same location where imaging line 162A is formed, to at least within the depth of field of line-scan camera unit 150A. FIG. 12 is a schematic diagram showing an example ceramic honeycomb structure mounted upon stage 112 and having an oval shaped perimeter 17.

Figure 13:
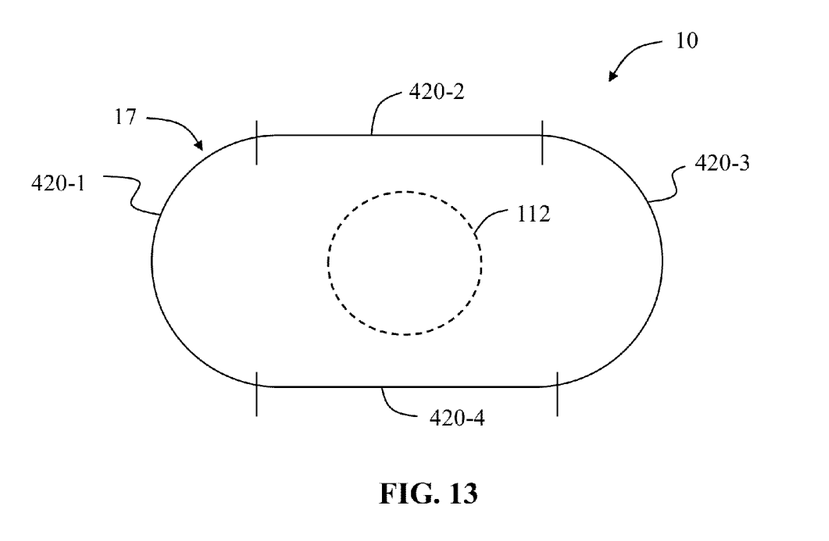
FIG. 13 is a top-down view of the ceramic honeycomb structure perimeter relative to the stage and showing how the perimeter can be divided up into arcs that are traced via a combination of translation and rotation imparted by the stage motion.

FIG. 13 is a top-down view of ceramic honeycomb structure perimeter 17 shown relative to stage 112 (dashed line). An example motion path that keeps skin 15 passing through a common point (or a small region) 410 as stage 112 rotates and translates ceramic honeycomb structure 10 is constructed out of four individual arcs 420-1, 420-2, 420-3 and 420-4 of perimeter 17. Each arc is traced by a combination of rotation 412 and translation 414, as illustrated schematically in FIG. 12. In some embodiments, certain contours require a stage motion that would include instantaneous acceleration if the motion were to be truly continuous. In such cases, controller 200 briefly interrupts the image acquisition process to accommodate one or more brief pauses in the movement of ceramic honeycomb structure 10 that are used to avoid instantaneous accelerations. In an example embodiment, controller 200 includes a database of known shapes for ceramic honeycomb structure perimeters 17 and the appropriate four-arc motion path is retrieved from that database.

While the disclosure has been described with respect to several preferred embodiments, various modifications and additions will become evident to persons of skill in the art. All such additions, variations and modifications are encompassed within the scope of the disclosure, which is limited only by the appended claims, and equivalents thereto.

What is claimed is:

1. A system for inspecting a ceramic honeycomb structure for at least one defect, wherein the ceramic honeycomb structure has an outer skin and opposite first and second endfaces having respective first and second perimeters, comprising:
    a movable stage that moves the ceramic honeycomb structure relative to a line-illumination of the outer skin, and first and second line illuminations of respective first and second endface portions including the respective first and second perimeters;
    a first line-scan camera that captures a first scanned image of the illuminated line portion of the outer skin onto a first detector;
    second and third line-scan cameras that capture respective second and third scanned images of the illuminated first and second endface portions, including the respective first and second perimeters, onto respective second and third detectors; and
    a controller operatively configured to control the movable stage to effectuate movement of the ceramic honeycomb structure and to receive the first, second and third scanned images and form therefrom a composite scanned image that shows the at least one defect.

2. The system of claim 1, further comprising first, second and third line illuminators configured to respectively form the first, second and third line illuminations, with each illuminator forming its associated line illumination by converging and overlapping two light beams.

3. The system of claim 1, wherein the first line-scan camera has an associated depth of field, wherein the honeycomb ceramic structure has an oval cross section, and wherein the movable stage is operable via the operation of the controller to move the oval honeycomb ceramic structure so that the outer skin is maintained within the depth of field.

4. The system of claim 1, further comprising a contour-imaging station configured to capture an image of one of the perimeters and send a signal representative of the captured perimeter image to the controller.

5. The system of claim 4, further comprising a height-measuring station that measures a relative height of the ceramic honeycomb structure and sends a signal representative of the measured height to the controller.

6. The system of claim 1, wherein the first line-scan camera unit has an image sensor comprising a linear array of pixels having a dimension of 6 μm.

7. The system of claim 1, wherein the second and third line-scan camera units respectively have an image sensor comprising a linear array of pixels having a dimension of 4 μm.

8. A method of inspecting a ceramic honeycomb structure for at least one defect, wherein the ceramic honeycomb structure has an outer skin and opposite first and second endfaces having respective first and second perimeters, comprising:
    capturing first digital line images of a line-illuminated portion of the outer skin as the ceramic honeycomb structure rotates to form a first scanned digital image of the outer skin;
    capturing second and third digital line images of illuminated first and second endface portions, including the respective first and second perimeters, as the ceramic honeycomb structure rotates to respectively form second and third scanned digital images of the first and second endface portions; and
    forming a composite image from the first, second and third scanned digital images; and
    identifying the at least one defect from the composite image.

9. The method of claim 8, wherein the line-illuminated portion is formed by two converging and overlapping light beams.

10. The method of claim 8, further comprising;
    capturing the first digital line images using a line-scan camera unit having an associated depth of field; and
    moving the ceramic honeycomb structure so that an imaged area of the skin stays within the depth of focus and perpendicular to a viewing direction of the line-scan camera unit.

11. The method of claim 10, wherein the ceramic honeycomb structure has a perimeter with an oval contour.

12. The method of claim 11, further comprising moving the honeycomb structure using a combination of rotation and translation over a motion path comprising four arcs.

13. The method of claim 10, wherein the composite image includes first and second edge-on views of the outer skin that respectively include first and second perimeters, and that includes identifying the at least one defect as being one of a skin-thickness variation and a skin-separation.

14. The method of claim 10, further comprising measuring a contour of the perimeter prior to capturing the digital line images.

15. A system for inspecting a ceramic honeycomb structure for at least one defect, wherein the ceramic honeycomb structure has an outer skin and opposite first and second endfaces having respective first and second perimeters, comprising:
- a first line-scan camera unit having a depth of field and that captures a first scanned image of a line-illuminated portion of the outer skin as the ceramic honeycomb structure rotates while maintaining the line-illuminated skin portion within the depth of field and perpendicular to a first-line-scan-camera viewing direction;
- second and third line-scan camera units to capture respective second and third scanned images of line-illuminated portions of the first and second endfaces, including the respective first and second perimeters, as the ceramic honeycomb structure rotates;
- a transport system to transport and rotate the ceramic honeycomb structure; and a controller operatively configured to control the transport system and to receive the first, second and third scanned images and form therefrom a composite scanned image that includes the at least one defect.

16. The system of claim 15, wherein the controller includes at least one of image analysis software and image processing software.

17. The system of claim 15, wherein the first line-scan camera unit includes a line-illumination system that forms two converging beams that overlap to form an illumination line that illuminates said line-illuminated portion.

18. The system of claim 15, further including a display for displaying at least one of the scanned images, a portion of the composite scanned image, and processed version of at least a portion of the scanned image, so as to display at least one defect in the ceramic honeycomb structure.

19. The system of claim 15, wherein the ceramic honeycomb structure has an oval perimeter contour, and wherein the controller is configured to drive the transport system along a motion path comprising four arcs formed by a combination of translation and rotation.

20. The system of claim 15, further comprising at least one of:
- a contour-imaging station configured to capture an image of one of the perimeters and send a signal representative of the captured perimeter image to the controller; and
- a height-measuring station that measures a relative height of the ceramic honeycomb structure and sends a signal representative of the measured height to the controller.

* * * * *